United States Patent [19]
Cronin et al.

[11] 3,966,936
[45] June 29, 1976

[54] PIPERAZINO QUINAZOLINE BRONCHODILATORS

[75] Inventors: Timothy H. Cronin, Niantic; Hans-Jürgen E. Hess, Old Lyme, both of Conn.

[73] Assignee: Pfizer Inc., New York, N.Y.

[22] Filed: May 29, 1975

[21] Appl. No.: 581,830

Related U.S. Application Data

[62] Division of Ser. No. 444,669, Feb. 21, 1974, Pat. No. 3,914,423, which is a division of Ser. No. 315,617, Dec. 15, 1972, Pat. No. 3,814,760, which is a division of Ser. No. 55,964, July 17, 1970, Pat. No. 3,723,434.

[52] U.S. Cl. ................................................. 424/251
[51] Int. Cl.² ........................................... A61K 31/505
[58] Field of Search .................................... 424/251

[56] References Cited
UNITED STATES PATENTS

| | | | |
|---|---|---|---|
| 2,593,798 | 4/1952 | Robinson | 260/268 BQ |
| 3,723,434 | 3/1973 | Cronin | 260/256.4 Q |

*Primary Examiner*—Norman A. Drezin
*Attorney, Agent, or Firm*—Connolly and Hutz

[57] ABSTRACT

A series of novel 4-piperazino-6,7-dialkoxyquinazolines and 1-piperazino-6,7-dialkoxyisoquinolines have been prepared, including their acid addition salts. These compounds are useful in therapy as bronchodilators and as smooth muscle relaxants. Methods for their preparation from known compounds are provided.

3 Claims, No Drawings

PIPERAZINO QUINAZOLINE BRONCHODILATORS

CROSS REFERENCE TO RELATED APPLICATIONS

This application is a division of application Ser. No. 444,669 filed Feb. 21, 1974, now U.S. Pat. No. 3,914,423 which is a division of application Ser. No. 315,617 filed Dec. 15, 1972, now U.S. Pat. No. 3,814,760 which is a division of application Ser. No. 55,964 filed July 17, 1970 and now U.S. Pat. No. 3,723,434.

BACKGROUND OF THE INVENTION

This invention relates to new and useful quinazoline and isoquinoline compounds. More particularly, it is concerned with a novel series of 4-piperazino-6,7-dialkoxyquinazolines and 1-piperazino-6,7-dialkoxyisoquinolines, which are of value in the field of medicine in view of their beneficial therapeutic effects.

In the past, various attempts have been made by a few investigators in the specialized field of organic medicinal chemistry to obtain new and useful bronchodilators, i.e., therapeutic agents which will cause bronchodilation without adversely affecting the treated subject. In one instance, this has involved the synthesis and testing of several 2- and 4-piperazino-6,7-dialkoxyquinazoline compounds, including the corresponding isoquinolines, such as those already disclosed in U.S. Pat. No. 3,517,005. However, in the search for still newer and better or more improved bronchodilators, little is known about the effect of certain 4-carbamyl substituents on the piperazine ring moiety of the aforesaid quinazoline and/or isoquinoline compounds in this area.

SUMMARY OF THE INVENTION

In accordance with the present invention, it has now been found that various novel dialkoxy quinazoline and isoquinoline compounds are surprisingly, extremely useful when employed in therapy as bronchodilators. More specifically, the novel compounds of this invention are all selected from the class of 4-piperazino-6,7-dialkoxyquinazoline and 1-piperazine-6,7-dialkoxyisoquinoline bases of the formula:

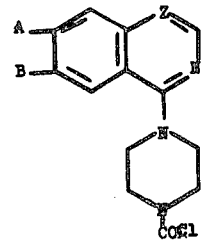

and the acid addition salts thereof, wherein A and B are each a member selected from the group consisting of methoxy and ethoxy; Z is a member selected from the group consisting of N and CH; and R is a member selected from the group consisting of hydroxypyrrolidino, piperidino, hydroxypiperidino and 4-methyl-4-hydroxypiperidino, said R being other than hydroxypyrrolidino when Z is N. These novel compounds are all useful in alleviating bronchoconstriction in afflicted subjects, in addition to simultaneously producing a smooth muscle relaxant effect.

Of especial interest in this connection are such typical and preferred member compounds of the invention as 4-(4-piperidinocarbonyl-1-piperazinyl)-6,7-dimethoxyquinazoline, 4-[4-(4-hydroxypiperidinocarbonyl)-1-piperazinyl]-6,7-dimethoxyquinazoline, 1-[4-(3-hydroxypyrrolidinocarbonyl)-1-piperazinyl]-6,7-dimethoxyisoquinoline, 1-(4-piperidinocarbonyl-1-piperazinyl)-6,7-dimethoxyisoquinoline, 1-[4-(3-hydroxypiperidinocarbonyl)-1-piperazinyl]-6,7-dimethoxyisoquinoline, 1-[4-(4-hydroxypiperidinocarbonyl)-1-piperazinyl]-6,7-dimethoxyisoquinoline and 1-[4-(4-methyl-4-hydroxypiperidinocarbonyl)-1-piperazinyl]-6,7-dimethoxyisoquinoline, and their hydrochloride acid addition salts. All these compounds effectively cause bronchodilation, as well as smooth muscle relaxation to occur in treated subjects to whom they are so administered at dose levels where no adverse side effects are clearly observed to be manifest. As a matter of fact, these compounds are even still less toxic than those quinazolines and isoquinolines already disclosed in aforesaid U.S. Pat. No. 3,517,005.

DETAILED DESCRIPTION OF THE INVENTION

In accordance with the process employed for preparing te novel compounds of this invention, a corresponding 4-(6,7-dialkoxyquinazolin-4-yl)piperazine-1-carbonyl chloride or 4-(6,7-dialkoxyisoquinolin-1-yl)-1-carbonyl chloride of the following general structural formula:

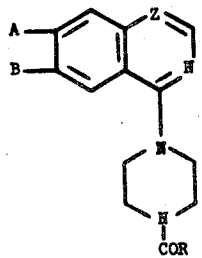

wherein A, B and Z are each as previously defined, is treated with an appropriate amine base of the formula RH, where R is as aforesaid, to form the desired 4-piperazino-6,7-dialkoxyquinazoline or 1-piperazino-6,7-dialkoxyisoquinoline final product, as the case may be. This particular reaction is normally carried out by using an excess of the amine base with respect to the required equimolar ratio, since this tends to shift the reaction equilibrium to the product side of the equation. In addition, excess amine can also function as a solvent for the reaction, with a preferred excess for these purposes being from about two to about ten moles of amine per one mole of carbonyl chloride intermediate. On the other hand, a reaction-inert organic solvent may also be used for the reaction and this would ordinarily entail employment of a cyclic ether such as dioxane or tetrahydrofuran, a halogenated hydrocarbon solvent like methylene chloride, chloroform, carbon tetrachloride, ethylene dichloride and s-tetrachloroethane, etc., or an aromatic hydrocarbon solvent such as benzene, toluene, xylene and the like, or even a N,N-dialkyl lower alkanoamide such as N,N-dimethylformamide, N,N-dimethylacetamide, N,N-diethylformamide and N,N-diethylacetamide, and so on. The temperature at which the reaction can be conducted varies widely within the range of from about 35°C. up to about 150°C. for a period of about one-half to about ten hours. A preferred reaction time and temperature for the process would be one that is approximately 65°-90°C. for about 1–2 hours. In the case where a particular solvent is used and/or the boiling point of the amine is below the desired reaction temperature range, it is often customary in practice to employ a sealed pressure bottle as the vessel in which to conduct the reaction. Upon completion of same, recovery of the desired product is readily effected by any number of conventional means. For instance, the solvent is first evaporated from the reaction mixture and the crude concentrate or resulting solid residue is thereafter taken up in or triturated with methylene chloride or similar organic solvent to remove any by-product impurities, followed by column chromatography if necessary. In this way, high yields of 4-piperazino-6,7-dialkoxyquinazoline or 1-piperazino-6,7-dialkoxyisoquinoline final product are thus obtained. It should be noted in this connection that te amines (RH) employed as reagent in the reaction are, for the most part, known compounds or else they can easily be prepared by those skilled in the art from readily available starting materials, using the standard techniques and/or conventional procedures of organic chemistry.

The 4-(6,7-dialkoxyquinazolin-4-yl)piperazine-1-carbonyl chloride and 4-(6,7-dialkoxyisoquinoline-1-yl)piperazine-1-carbonyl chloride intermediates, on the other hand, which are used as the principal or major starting materials in the herein described process of this invention, are themselves new compounds here prepared for the first time in the art. These particular compounds are prepared by treating the corresponding known 4-piperazinyl-6,7-dialkoxyquinazoline or 1-piperazinyl-6,7-dialkoxyisoquinoline compounds (described in U.S. Pat. No. 3,517,005) with at least an equimolar amount of phosgene and preferably, from about one to about five moles of same, in a reaction-inert organic solvent of the same type employed in the previously described final step. The temperature for this reaction will vary from about 10°C. to about 65°C. for a period of about one to about 24 hours, and it is normally conducted in the presence of a suitable organic base of sufficient strength to neutralize the hydrogen chloride byproduct. Preferred organic bases for use in this connection include tertiary amines like triethylamine, N,N-dimethylaniline, pyridine and quinoline, etc. Upon completion of the reaction, the desired intermediate is readily obtained using standard techniques to isolate the product in pure crystalline form. For example, this may be readily accomplished by first removing the insoluble amine acid addition salt from the mixture via filtration and thereafter evaporating the solvent filtrate to near dryness, followed by column chromatography to obtain the pure compound.

An alternate and preferred method of synthesis for preparing the novel compounds of this invention involves treating an appropriate 4-halo-6,7-dialkoxyquinazoline or 1-halo-6,7-dialkoxyisoquinoline, as the case may be, with an amine base of the formula:

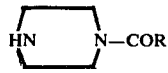

where R is as previously defined, and the halogen of the starting material is either chlorine or bromine. This particular reaction is normally carried out by using an excess of the amine base with respect to the required equimolar ratio, since this serves to shift the reaction equilibrium to the product side of the equation. In addition, the excess amine can also function as a solvent for the reaction, with a preferred excess for these purposes being from about two to about ten moles of amine per one mole of halogen starting material. On the other hand, a reaction-inert polar organic solvent may also be used for the reaction and this would ordinarily entail employment of a cyclic ether such as dioxane and tetrahydrofuran, or a lower dialkylsulfoxide such as dimethyl and diethylsulfoxide, or a lower alkanol solvent like methanol, ethanol or isoamyl alcohol, etc. or even a N,N-dialkyl lower alkanoamide such as N,N-dimethylformamide, N,N-dimethylacetamide, N,N-diethylformamide and the like. The temperature at which the reaction can be conducted varies widely within the range of from about 50°C. up to about 200°C. for a period of about one to about twelve hours. A preferred reaction time and temperature for the process at hand would be about 120°-150°C. for about 2-4 hours. In the case where a particular solvent is used and/or the boiling point of the amine is below the desired reaction temperature range, it is often customary in practice to employ a sealed pressure bottle as the proper vessel in which to conduct the reaction. Upon completion of same, recovery of the desired product is readily effected by any number of conventional means. For instance, the solvent is evaporated from the mixture and the crude concentrate or resulting solid residue is thereafter triturated with ethyl acetate or similar organic solvent. In this way, high yields of the desired final product are thus obtained. It should be noted in this connection that the amines employed as reagent in this reaction, such as 1-(piperidinocarbonyl)piperazine, are all new compounds which can easily be prepared by those skilled in the art from readily available starting materials, using the standard procedures of organic chemistry.

Inasmuch as the 4-piperazino-6,7-dialkoxyquinazoline and 1-piperazino-6,7-dialkoxyisoquinoline compounds of this invention are basic compounds, they are capable of forming a wide variety of different salts with various inorganic and organic acids. Although such salts must first be pharmaceutically acceptable for administration to animals, it is often convenient in practice to initially isolate the desired organic base compound from the reaction mixture as a pharmaceutically unacceptable salt and then simply convert the latter back to the free base compound by treatment with an alkaline reagent and thereafter subsequently convert the latter free base to a pharmaceutically acceptable acid addition salt. The acid addition salts of the aforesaid novel dialkoxy quinazoline and isoquinoline base compounds of this invention are readily prepared by treating the base compound with an equivalent amount of the chosen acid in an aqueous solution or in a suitable organic solvent, such as methanol or ethanol. Upon evaporation of the solvent, the desired solid salt is obtained.

The acids which are used to prepare the pharmaceutically acceptable acid addition salts of the aforementioned 4-piperazino-6,7-dialkoxyquinazoline and 1-piperazino-6,7-dialkoxyisoquinoline base compounds of this invention are those which form non-toxic acid addition salts, i.e., salts containing pharmacologically acceptable anions such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, methanesulfonate, ethanesulfonate, benzenesulfonate, p-toluenesulfonate and pamoate (i.e., 1,1-methylene-bis-2-hydroxy-3-naphthoate) salts.

As previously indicated, the 4-piperazino-6,7-dialkoxyquinazoline and 1-piperazino-6,7-dialkoxyisoquinoline compounds of the present invention are all readily adapted to therapeutic use as bronchodilators, particularly in view of their ability to relieve bronchoconstriction in afflicted subjects to a statistically significant degree, in addition to effecting smooth muscle relaxation. For instance, 1-(4-piperidinocarbonyl-1-piperazinyl)-6,7-dimethoxyisoquinoline, a typical and preferred agent of the present invention, has been found to afford excellent protection (up to about 60%), as a bronchodilator, against the effects of histamine aerosol challenge in conscious guinea pigs when the drug is given orally to said animals at a dose test level of 60 mg./kg. at a period just one hour prior to challenge. Additionally, none of these compounds cause any substantial side effects to occur in the subject to whom they are so administered, i.e., no problems of toxicity or of an untoward pharmacological nature, either gross or microscopic, are ever encountered when said compounds are administered for the aforesaid purpose in the manner described as indicated above.

In accordance with a method of treatment of the present invention, the herein described 4-piperazino-6,7-dialkoxyquinazoline and 1-piperazino-6,7-dialkoxyisoquinoline bronchodilators can be administered to an afflicted subject via either the oral or parenteral routes of administration. In general, these compounds are most desirably administered in doses ranging from about 25 mg. up to about 1.0 g. per day, although variations will still necessarily occur depending upon the weight of the subject being treated. However, a dosage level that is in the range of from about 0.40 mg. to about 16 mg. per kg. of body weight per day is most desirably employed in order to achieve effective results. Nevertheless, it is still to be appreciated that other variations may also occur in this respect, depending upon the species of animal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur provided that such higher dose levels are first divided into several smaller doses that are to be administered throughout the day.

In connection with the use of the 4-piperazino-6,7-dialkoxyquinazoline and 1-piperazino-6,7-dialkoxyisoquinoline compounds of this invention for the treatment of subjects afflicted with bronchoconstriction, it is to be noted that they may be administered either alone or in combination with pharmaceutically acceptable carriers by either of the routes previously indicated, and that such administration can be carried out in both single and multiple dosages. More particularly, the novel compounds of the invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with such binding agents as polyvinylpyrrolidine, sucrose, gelatin and acacia. Additionally, lubricating agents such as magnesium stearate, sodium lauryl sulfate and talc are very often useful for tabletting purposes. Solid compositions of a similar type may also be employed as fillers in soft and hard-filled gelatin capsules. Preferred materials in the connection would also include lactose or milk sugar, as well as high molecular weight polyethylene glycols. When aqueous suspensions and/or elixirs are desired for oral administration, the essential active ingredient therein may be combined with various sweetening or flavoring agents, coloring matter or dyes, and, if so desired, emulsifying and/or suspending agents as well, together with such diluents as water, ethanol, propylene glycol, glycerin and various like combinations thereof.

For purposes of parenteral administration, solutions of these particular 4-piperazino-6,7-dialkoxyquinazolines and 1-piperazino-6,7-dialkoxyisoquinolines in either sesame or peanut oil or in aqueous propylene glycol may be employed, as well as sterile aqueous solutions of the corresponding water-soluble, non-toxic mineral and organic acid addition salts previously enumerated. Such aqueous solutions should be suitably buffered if necessary and the liquid dilent first rendered isotonic with sufficient saline or glucose. These particular solutions are especially suitable for intravenous, intramuscular and subcutaneous injection purposes.

EXAMPLE I

To a solution consisting of 12.4 g. (0.124 mole) of phosgene dissolved in 50 ml. of toluene, there was added in a dropwise manner during the course of a 30-minute period a solution containing 26.0 g. (0.095 mole) of 4-piperazinyl-6,7-dimethoxyquinazoline (prepared as described in U.S. Pat. No. 3,517,005), 9.9 g. (0.115 mole) of pyridine, 180 ml. of toluene and 160 ml. of methylene chloride. Upon completion of the addition step, during which time a slight exothermic reaction had occurred, the resultant crystalline yellow slurry was stirred at room temperature (~25°C.) for a period of 20 hours. The solid product obtained in this manner was recovered by means of filtration and then partitioned between 500 ml. of saturated aqueous sodium bicarbonate and 300 ml. of methylene chloride. After further extracting the aqueous phase with three-200 ml. portions of methylene chloride, the organic extracts were combined, dried over anhydrous sodium sulfate and filtered, and the resulting clear filtrate subsequently evaporated to dryness while under reduced pressure. The residual solid materil (28.0 g.) was then charged in methylene chloride solution on a 400 mm. × 300 mm. column of silica gel and eluted with 600 ml. of ethyl acetate. Under evaporation of the eluate, there was obtained a 13.1 g. (41%) yield of analytically pure 4-(6,7-dimethoxyquinazoline-4-yl)piperazine-1-carbonyl chloride, m.p. 162°–164°C. (dec.).

Anal. Calcd. for $C_{15}H_{17}ClN_4O_3$: C, 53.49; H, 5.09; N, 16.64; Cl, 10.53. Found: C, 53.49; H, 5.15; N, 16.52; Cl, 10.41.

EXAMPLE II

The procedure described in Example I is repeated except that 4-piperazinyl-6,7-diethoxyquinazoline is the starting material employed in place of the corresponding dimethoxy quinazoline. In this particular case, the corresponding final product obtained is 4-(6,7-diethoxyquinazoline-4-yl)piperazine-1-carbonyl chloride.

EXAMPLE III

To a cold, well-stirred solution consisting of 50.0 g. (0.183 mole) of 1-piperazinyl-6,7-dimethoxyisoquinoline (prepared as described in U.S. Pat. No. 3,517,005) dissolved in 500 ml. of methylene chloride, there was introduced a stream of phosgene gas for a period of 30 minutes. Precipitation occurred soon after the first eight minutes, followed by clearing and complete solution at the 25-minute mark. Upon completion of this step, the resulting solution was then concentrated in vacuo and 500 ml. of methylene chloride thereafter added to effect the formation of a new crystalline slurry. After removing the solid material by means of filtration, the filtrate was collected and subsequently passed through a 400 mm. × 50 mm. column of Florisil (registered trademark name of the Floridin Company of Tallahasee, Florida of synthetic magnesia-silica gel ion-exchange material) which was thereafter eluted with 1500 ml. of ethyl acetate. The combined eluates obtained in this manner then gave, after evaporation to dryness, 30 g. (49%) of 4-(6,7-dimethoxyisoquinoline-1-yl)-piperazine-1-carbonyl chloride as a white crystalline material, m.p. 162°–164°C. (dec.).

Anal. Calcd. for $C_{15}H_{17}ClN_4O_3$: C, 65.60; H, 7.34; N, 14.57. Found: C, 65.57; H, 7.37; N, 14.35.

EXAMPLE IV

The procedure described in Example III is followed except that 1-piperazinyl-6,7-diethoxyisoquinoline is the starting material employed in place of the corresponding dimethoxy isoquinoline. In this particular case, the corresponding final product obtained is 4-(6,7-diethoxyisoquinolin-1-yl)piperazine-1-carbonyl chloride.

EXAMPLE V

A solution consisting of 1.5 g. (0.004 mole) of 4-(6,7-dimethoxyquinazolin-4-yl)piperazine-1-carbonyl chloride, prepared as described in Example I, and 1.15 g. (0.0135 mole) of piperidine dissolved in 75 ml. of benzene was stirred under reflux for a period of one hour. The resulting solution was then concentrated in vacuo to remove the benzene and the residue dissolved in 100 ml. of methylene chloride. After washing the latter solution with two-50 ml. portions of water, the organic layers were combined and subsequently dried over anhydrous sodium sulfate. The clear filtrate was then concentrated in vacuo and charged onto a column packed with silica gel, followed by subsequent elution with a 150 ml. portion of ethyl acetate-methanol (9:1 by volume). Upon careful evaporation of the resulting eluate, there was ultimately obtained a 0.84 g. (48.5%) yield of analytically pure 4-(4-piperidinocarbonyl-1-piperazinyl)-6,7-dimethoxyquinazoline, m.p. 179°–180°C.

Anal. Calcd. for $C_{20}H_{27}N_5O_3$: C, 62.32; H, 7.06; N, 18.71. Found: C, 62.21; H, 7.31; N, 17.91.

EXAMPLE VI

A solution consisting of 1.0 g. (0.003 mole) of 4-(6,7-dimethoxyisoquinolin-1-yl)piperazine-1-carbonyl chloride, prepared as described in Example III, and 0.765 g. (0.009 mole) of piperidine dissolved in 50 ml. of benzene was stirred under reflux for a period of one hour. The reaction mixture was then concentrated to near dryness while under reduced pressure and the resulting residue subsequently dissolved in 50 ml. of chloroform. After washing the chloroform solution with two-50 ml. portions of water and drying over anhydrous sodium sulfate, the dried chloroform extract was recovered as the filtrate and thereafter evaporated to dryness to give a crystalline product as the residue. Recrystallization of the latter material from ethyl acetate-hexane then gave 0.75 g. (65%) of pure 1-(4-piperadinocarbonyl-1-piperazinyl)-6,7-dimethoxyisoquinoline as a white crystalline solid, m.p. 157°–158°C.

Anal. Calcd. for $C_{21}H_{28}N_4O$: C, 65.60; H, 7.34; N, 14.57. Found: C, 65.57; H, 7.37; N, 14.35.

EXAMPLE VII

The procedure described in Example V was repeated to prepare the following 4-piperazino-6,7-dimethoxyquinazoline and 1-piperazino-6,7-dimethoxyisoquinoline bases, respectively, starting from either 4-(6,7-dimethoxyquinazolin-4-yl)piperazine-1-carbonyl chloride or 4-(6,7-dimethoxyisoquinolin-1-yl)piperazine-1-carbonyl chloride, as the case may be, and the appropriate primary or secondary organic amine reagent in each instance.

4-[4-(3-hydroxypiperidinocarbonyl)-1-piperazinyl]-6,7-dimethoxyquinazoline, m.p. 211°–212°C.

1-[4-(3-hydroxypyrrolidinocarbonyl)-1-piperazinyl]-6,7-dimethoxyisoquinoline, m.p. 155°–156°C.

1-[4-(3-hydroxypiperidinocarbonyl)-1-piperazinyl]-6,7-dimethoxyisoquinoline, m.p. 161°–161.5°C.

1-[4-(4-hydroxypiperidinocarbonyl)-1-piperazinyl]-6,7-dimethoxyisoquinoline, m.p. 171°–172°C.

1-[4-(4-methyl-4-hydroxypiperidinocarbonyl)-1-piperazinyl]-6,7-dimethoxyisoquinoline, m.p. 184°–185°C.

EXAMPLE VIII

The procedure described in Example V is employed again to prepare the following 4-piperazino-6,7-dialkoxyquinazoline base compounds, starting from the corresponding 4-(6,7-dialkoxyquinazolin-4-yl)piperazine-1-carbonyl chloride and the appropriate organic amine reagent in each instance:

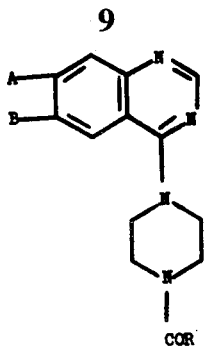

| A | B | R |
|---|---|---|
| $OC_2H_5$ | $OC_2H_5$ | piperidino |
| $OC_2H_5$ | $OC_2H_5$ | 4-hydroxypiperidino |
| $OCH_3$ | $OCH_3$ | 3-hydroxypiperidino |
| $OC_2H_5$ | $OC_2H_5$ | 3-hydroxypiperidino |
| $OCH_3$ | $OCH_3$ | 2-hydroxypiperidino |
| $OC_2H_5$ | $OC_2H_5$ | 2-hydroxypiperidino |
| $OCH_3$ | $OCH_3$ | 4-methyl-4-hydroxypiperidino |
| $OC_2H_5$ | $OC_2H_5$ | 4-methyl-4-hydroxypiperidino |

EXAMPLE IX

The procedure described in Example V is employed once again to prepare the following 1-piperazino-6,7-dialkoxyisoquinoline base compounds, starting from the corresponding 4-(6,7-dialkoxyisoquinolin-1-yl)piperazine-1-carbonyl chloride and the appropriate organic amine reagent in each instance:

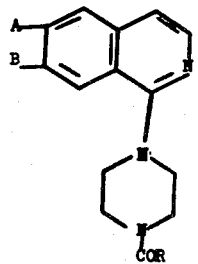

| A | B | R |
|---|---|---|
| $OC_2H_5$ | $OC_2H_5$ | piperidino |
| $OCH_3$ | $OCH_3$ | 2-hydroxypyrrolidino |
| $OC_2H_5$ | $OC_2H_5$ | 2-hyroxypiperidino |
| $OC_2H_5$ | $OC_2H_5$ | 3-hyroxypyrrolidino |
| $OC_2H_5$ | $OC_2H_5$ | 4-hydroxypiperidino |
| $OC_2H_5$ | $OC_2H_5$ | 3-hydroxypiperidino |
| $OCH_3$ | $OCH_3$ | 2-hydroxypiperidino |
| $OC_2H_5$ | $OC_2H_5$ | 2-hydroxypiperidino |
| $OC_2H_5$ | $OC_2H_5$ | 4-methyl-4-hydroxypiperidino |

EXAMPLE X

The hydrohalide acid addition salts of the 4-piperazino-6,7-dialkoxyquinazoline and 1-piperazino-6,7-dialkoxyisoquinoline base compounds of this invention reported previously, such as the corresponding hydrochloride, hydrobromide and hydriodide salts, are each individually prepared by first dissolving the respective organic base compound in absolute ether and then adding a saturated solution of the appropriate hydrohalide gas in ethyl acetate to the aforementioned ethereal solution, whereupon the desired acid addition salt soon precipitates from said solution. In this way, 500 mg. of 1-(4-piperidinocarbonyl-1-piperazinyl)-6,7-dimethoxyisoquinoline is converted via dry hydrogen chloride gas to the corresponding hydrochloride acid addition salt (m.p. 198°–199°C.) in almost quantitative yield.

EXAMPLE XI

The nitrate, sulfate or bisulfate, phosphate or acid phosphate, acetate, lactate, citrate or acid citrate, tartrate or bitartrate, succinate, maleate, fumarate, methanesulfonate, ethanesulfonate, benzenesulfonate, p-toluenesulfonate and pamoate (i.e., 1,1-methylene-bis-2-hydroxy-3-naphthoate) salts of each of the aforementioned 4-piperazino-6,7-dialkoxyquinazoline and 1-piperazino-6,7-dialkoxyisoquinoline base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition salt therefrom. In this manner, equimolar amounts of 4-(4-piperidinocarbonyl-1-piperazinyl)-6,7-dimethoxyquinazoline and concentrated sulfuric acid react to afford the corresponding sulfuric acid addition salt. In like manner, each of the other salts is also similarly prepared.

EXAMPLE XII

A dry solid pharmaceutical composition is prepared by combining the following materials together in the proportions by weight indicated below:

| | |
|---|---|
| 1-(4-Piperidinocarbonyl-1-piperazinyl)-6,7-dimethoxy-isoquinoline hydrochloride | 50 |
| Sodium citrate | 25 |
| Alginic acid | 10 |
| Polyvinylpyrrolidone | 10 |
| Magnesium stearate | 5 |

After the dried mixture is thoroughly blended, tablets are punched from the resulting mixture, each tablet being of such size that it contains 50 mg. of the active ingredient. Other tablets are also prepared in a similar manner containing 5, 10 and 25 mg. of the active ingredient, respectively, by merely using the appropriate amount of the dialkoxy isoquinoline compound in each case.

EXAMPLE XIII

A dry solid pharmaceutical composition is prepared by combining the following materials together in the properties by weight indicated below:

| | |
|---|---|
| 1-(4-Piperidinocarbonyl-1-piperazinyl)-6,7-dimethoxy-isoquinoline hydrochloride | 50 |
| Calcium carbonate | 20 |
| Polyethyl glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 100 mg. of the active ingredient.

EXAMPLE XIV

The following 1-piperazino-6,7-dimethoxyisoquinolines were tested for bronchodilator activity in conscious female guinea pigs by the procedure described in U.S. Pat. No. 3,517,005. The compounds were given orally at 60 mg./kg., followed by a histamine aerosol challenge one hour later. The results obtained in this manner are expressed below in terms of percent protection afforded by the test compound as compared to the control (i.e., saline solution with no compound):

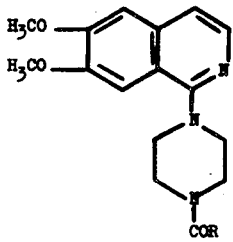

| R | % Protection |
| --- | --- |
| 3-hydroxypyrrolidino | 59 |
| 3-hydroxypiperidino | 39 |
| 4-hydroxypiperidino | 47 |
| 4-methyl-4-hydroxypiperidino | 53 |
| piperidino | 55 |

EXAMPLE XV

The test procedure employed in the previous example was repeated again to determine the bronchodilator activity of the following 4-piperazino-6,7-dimethoxyaquinazolines, and the results obtained in this manner are reported below in the usual tabular form:

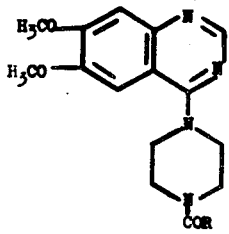

| R | % Protection |
| --- | --- |
| piperidino | 47 |
| 4-hydroxypiperidino | 27 |

EXAMPLE XVI

A 22-liter round-bottomed flask was charged with 861.4 g. (10.0 moles) of anhydrous piperazine and 8.6 liters of dry benzene. The resulting solution was stirred at 40°C., while 738.0 g. (5.0 moles) of 1-(chlorocarbonyl)piperidine were slowly added from a dropping funnel during the course of a one-hour period, with the temperature of the mixture being maintained in the 40°–50°C. range throughout the entire addition step. The resulting slurry, which now contained precipitated piperazine hydrochloride as by-product, was stirred for an additional two hours at ambient temperatures and then chilled to 20°C. The crystalline material was then removed by means of filtration, and the filter cake so obtained was thereafter washed with a fresh portion of cold benzene. The filtrate and washings were combined and subsequently concentrated in vacuo to afford a residual oil that was thereafter triturated with four liters of boiling hexane. The insoluble material that formed at this point was then removed by means of suction filtration and the resulting filtrate was thereafter further concentrated in vacuo to a volume of ca. 2 liters, followed by chilling to 20°C. to give another crystalline slurry. Upon filtration of the latter material followed by washing with hexane, there were obtained 703 g. of crude product, which was immediately reslurried in four liters of boiling hexane for an additional period of ten minutes. The small amount of insoluble material present was then removed by means of filtration, and the clear filtrate was subsequently concentrated in vacuo to a total volume of ca. 2 liters and then chilled to 5°C. The pure product was recovered by means of suction filtration and after air-drying to constant weight, there were ultimately obtained 592 g. (60%) of 1-(piperidinocarbonyl)-piperazine, m.p. 77°–79°C.

EXAMPLE XVII

A 22-liter round-bottomed flask was charged with 922.5 g. (4.13 moles) of 1-chloro-6,7-dimethoxyisoquinoline (prepared as described in U.S. Pat. No. 3,517,005), 1054.5 g. of 1-(piperidinocarbonyl)piperazine and 12 liters of dry isoamyl alcohol. The resulting mixture was heated in order to effect solution and the solution stirred at 130°C. for a period of 18 hours. At the end of this time, the reaction mixture was concentrated in vacuo, until most of the alcohol was subsequently removed therefrom, and the resulting concentrate thereafter diluted with 4 liters of cold water, 8 liters of methylene chloride and 404.0 g. (4.0 moles) of triethylamine. The different layers were then separated at this point and the methylene chloride layer was subsequently washed twice with two fresh 4-liter portions of cold water. After drying the latter solution over anhydrous magnesium sulfate and filtering the mixture, there was obtained a clear dry filtrate that was subsequently concentrated in vacuo while hexane was slowly being added thereto. When all of the methylene chloride had been displaced from the system, the total volume of the hexane slurry was taken up to ca. 7 liters with additional portions of fresh hexane solvent. The crystalline material obtained in this manner was then collected by means of suction filtration, and the filter cake so obtained subsequently washed with hexane and air-dired to constant weight. After further drying at 55°C. for 18 hours, there were ultimately obtained 1370 g. of crude product, m.p. 149°–152°C.

The crude product obtained above (1370 g.) was then taken up in ca. 10 liters of methylene chloride and subsequently treated with 500 g. of Darco G-60 (registered trademark name of the Atlas Powder Company of Wilmington, Del., for an activated carbon normally used in chromatographic analysis having an average particle size that is 60–70% less than 325 mesh) to give a clear filtrate. The latter solution was then concentrated in vacuo and the product precipitated by addition of hexane to yield 1300 g. of material, m.p. 151°–153°C. Recrystallization of the latter purified material was then accomplished by dissolving same in 13 liters of boiling acetone, treating the hot solution with Darco G-10, followed by filtration and subsequent concentration of the resulting filtrate in vacuo to a final volume of ca. 3 liters. The crystalline slurry thus obtained was then chilled to 0°C. and filtered to give as the final product 1008 g. (68%) of pure 1-(4-piperidinocarbonyl-1-piperazinyl)-6,7-dimethoxyisoquinoline, m.p. 153°–155°C. This material was identical in every respect with the product of Example VI.

EXAMPLE XVIII

The procedure described in the previous example is repeated again except that 1-bromo-6,7-dimethoxyisoquinoline is employed as starting material for the reaction in place of the corresponding chloro compound used before. Again, the final product obtained is 1-(4-piperidinocarbonyl-1-piperazinyl)-6,7-dimethoxyisoquinoline, identical in every respect with the product previously reported in Examples VI and XVII.

In like manner, 1-chloro-6,7-diethoxyisoquinoline and 1-(piperidinocarbonyl)piperazine react to afford 1-(4-piperidinocarbonyl-1-piperazinyl)-6,7-diethoxyisoquinoline, while 4-chloro-6,7-dimethoxyquinazoline and 1-(piperidinocarbonyl)piperazine react to afford 4-(4-piperidinocarbonyl-1-piperazinyl)-6,7-dimethoxyquinazoline respectively. The latter compound is, of course, identical in every respect with the product of Example V.

What is claimed is:

1. A method for effecting bronchodilator action in a subject afflicted with bronchoconstriction, which comprises administering to said subject an effective amount of a compound selected from the group consisting of 4-piperazino-6,7-dialkoxyquinazoline bases of the formula:

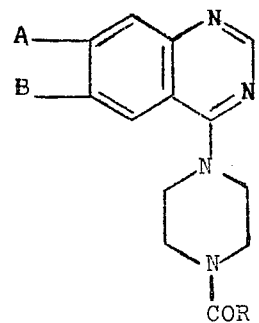

and the pharmaceutically acceptable addition salts thereof, wherein A and B are each a member selected from the group consisting of methoxy and ethoxy, and R is a member selected from the group consisting of piperidino, hydroxypiperidino and 4-methyl-4-hydroxypiperidino.

2. The method as claimed in claim 1 wherein the compound administered is 4-(4-piperidinocarbonyl-1-piperazinyl)-6,7-dimethoxyquinazoline.

3. The method as claimed in claim 1 wherein the compound administered is 4-[4-(4-hydroxypiperidinocarbonyl)-1-piperazinyl]-6,7-dimethoxyquinazoline.

* * * * *